United States Patent [19]

Grasselli et al.

[11] Patent Number: 5,430,210
[45] Date of Patent: Jul. 4, 1995

[54] SELECTIVE HYDROGEN COMBUSTION PROCESSES

[75] Inventors: Robert K. Grasselli, Chadds Ford, Pa.; John G. Tsikoyiannis, Princeton, N.J.

[73] Assignee: Mobil Oil Corporation, Fairfax, Va.

[21] Appl. No.: 272,347

[22] Filed: Jul. 8, 1994

Related U.S. Application Data

[63] Continuation-in-part of Ser. No. 112,287, Aug. 27, 1993.

[51] Int. Cl.$^6$ .......................... C07C 1/00; C07C 5/327
[52] U.S. Cl. ................................. 585/315; 585/324; 585/654
[58] Field of Search .......................... 585/315, 324, 654

[56] References Cited

U.S. PATENT DOCUMENTS

| | | | |
|---|---|---|---|
| 3,136,713 | 6/1964 | Miale et al. | 208/113 |
| 3,254,023 | 5/1966 | Miale et al. | 208/120 |
| 3,267,023 | 8/1966 | Miale et al. | 208/111 |
| 3,450,500 | 6/1969 | Setzer et al. | 23/212 |
| 3,501,547 | 3/1970 | Nolan et al. | 260/680 |
| 3,760,024 | 9/1973 | Cattanach | 260/673 |
| 3,845,150 | 10/1974 | Yan et al. | 260/673.5 |
| 3,937,748 | 2/1976 | Miklas | 260/680 E |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,435,607 | 3/1984 | Imai | 585/443 |
| 4,652,687 | 3/1987 | Imai et al. | 585/319 |
| 4,691,071 | 9/1987 | Bricker | 585/319 |
| 4,727,216 | 2/1988 | Miller | 585/660 |
| 4,739,124 | 4/1988 | Ward | 585/658 |
| 4,754,095 | 6/1988 | Coughenour et al. | 585/500 |
| 4,788,371 | 11/1988 | Imai et al. | 585/443 |
| 4,791,079 | 12/1988 | Hazbun | 502/4 |
| 4,806,624 | 2/1989 | Herber et al. | 585/440 |
| 4,827,066 | 5/1989 | Herber et al. | 585/319 |
| 4,827,071 | 5/1989 | Hazbun | 585/443 |
| 4,902,849 | 2/1990 | McKay et al. | 585/660 |
| 4,921,828 | 5/1990 | Brazdil et al. | 502/205 |
| 4,940,826 | 7/1990 | Freide et al. | 585/600 |
| 4,990,714 | 2/1991 | Nemet-Mavrodin | 585/407 |
| 5,071,814 | 12/1991 | Sasaki et al. | 502/205 |
| 5,086,032 | 2/1992 | Mazzocchia et al. | 502/315 |
| 5,276,237 | 1/1994 | Mieville | 585/500 |

FOREIGN PATENT DOCUMENTS

568303A2 11/1993 European Pat. Off.
2190397 11/1987 United Kingdom.

OTHER PUBLICATIONS

Shu, J. et al., Canadian Journal of Chemical Engineering, vol. 69, 1036–1060 (1991).
Ziaka, Z. D. et al., "A High Temperature Catalytic Membrane Reactor for Propane Dehydrogenation" J. of Membrane Science, 77, 221–232 (1993).
Cosimo, R. D. et al., "Oxidative Dehydrodimerization of Propylene over a $Bi_2O_3$-$La_2O_3$ Oxide Ion-Conductive Catalyst" Journal of Catalysis 102, 234–239 (1986).
Gellings, P. J. et al., "Ion and Mixed Conducting Oxides as Catalysts" Catalysis Today 12, 1–105 (1992).
Burggraaf, A. J. et al., "Recent Development in Oxygen-Ion Conducting Solid Electrolyte and Electrode Materials," Adv. Solid State Chemistry, vol. 1 259–293 (1989).

Primary Examiner—Anthony McFarlane
Assistant Examiner—Nhat D. Phan
Attorney, Agent, or Firm—Alexander J. McKillop; Dennis P. Santini; Lori F. Cuomo

[57] ABSTRACT

There is provided a process for the selective combustion of hydrogen using a membrane structure containing metal oxides, such as bismuth oxide, that can selectively oxidize hydrogen in the presence of hydrocarbons by virtue of their lattice oxygen. A hydrocarbon/hydrogen containing gas and an oxygen-containing gas, such as air, are passed on separate sides of the membrane. The lattice oxygen is continuously being replenished by air oxidation. The selective hydrogen combustion reactor can be used in dehydrogenation processes as an interstage heater and as a hydrogen scavenger for olefin yield maximization.

41 Claims, 1 Drawing Sheet

SELECTIVE HYDROGEN COMBUSTION PROCESSES

CROSS REFERENCE TO RELATED APPLICATIONS

This application is a continuation-in-part of application Ser. No. 08/112,287, filed Aug. 27, 1993.

BACKGROUND

There is provided a selective hydrogen combustion reactor and processes for using the same. There is further provided a process for the net catalytic oxidative dehydrogenation of alkanes to produce alkenes. The process involves simultaneous equilibrium dehydrogenation of alkanes to alkenes and selective combustion of the hydrogen formed to drive the equilibrium dehydrogenation reaction further to the product alkenes.

Developments in zeolite catalysts and hydrocarbon conversion processes have created interest in utilizing light aliphatic feedstocks for producing $C_{5+}$ gasoline, diesel fuel, etc. In addition to chemical reactions promoted by medium-pore zeolite catalysts, a number of discoveries have contributed to the development of new industrial processes. These are safe, environmentally acceptable processes for utilizing aliphatic feedstocks. Conversions of $C_2$-$C_4$ alkenes and alkanes to produce aromatics-rich liquid hydrocarbon products were found by Cattanach (U.S. Pat. No. 3,760,024) and Yan et al. (U.S. Pat. No. 3,845,150) to be effective processes using the zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640; and 4,227,992. The above-identified disclosures are incorporated herein by reference.

Catalytic dehydrogenation and aromatization of light paraffinic streams, e.g., $C_2$-$C_4$ paraffins, commonly referred to as LPG, is strongly endothermic and typically carried out at temperatures between 540° and 820° C. (1000° and 1500° F.), the problem of transferring sufficient heat to a catalytic reaction zone to carry out the paraffin upgrading reaction remains as a serious challenge to commercialization of these processes.

Dehydrogenation of paraffins to olefins has recently generated increasing interest as the market value of olefinic intermediate feedstocks continues to rise. Light olefins, particularly $C_2$-$C_4$ olefins, enjoy strong demand as building blocks for a wide range of valuable end products including fuels and specialized lubricants as well as thermoplastics.

Methods for supplying heat to an endothermic reaction zone include indirect heat exchange as well as direct heat exchange. Indirect heat exchange is exemplified by a multi-bed reactor with inter-bed heating or a fluid bed reactor with heat exchange coils positioned within the catalyst bed. Direct heat exchange techniques include circulation of inert or catalytically active particles from a high temperature heat source to the reaction zone, or the coupling of a secondary exothermic reaction with the primary endothermic reaction in a single catalytic reaction zone. Examples of such secondary exothermic reactions include (1) oxidative dehydrogenation of a portion of the feedstream, (2) sacrificial co-combustion of a part of the alkane/alkene mixture, and (3) combustion of carbonized species (e.g., coke) on the catalyst.

Currently known techniques for oxidative dehydrogenation are unfortunately not selective enough to achieve sufficiently high levels to allow for commercial practice and at least a part of the valuable product is over-oxidized, usually to the waste products, CO, $CO_2$, and $H_2O$.

Examples of such sacrificial co-combustion processes include those described in U.S. Pat. No. 3,136,713 to Miale et al. which teaches a method for heating a reaction zone by selectively burning a portion of a combustible feedstream in a reaction zone. Heat is directly transferred from the exothermic oxidation reaction to supply the endothermic heat for the desired conversion reaction.

A process for the oxidative dehydrogenation of propane is described in U.S. Pat. No. 5,086,032 to Mazzocchia et al.

Heat balanced reactions are also taught in U.S. Pat. Nos. 3,254,023 and 3,267,023 to Miale et al. Additionally, U.S. Pat. No. 3,845,150 to Yan and Zahner teaches a heat balanced process for the aromatization of hydrocarbon streams by combining the exothermic aromatization of light olefins with the endothermic aromatization of saturated hydrocarbons in the presence of a medium-pore zeolite catalyst.

Turning now to chemical reaction thermodynamics, it is well recognized that the extent of reaction may be increased by removing reaction products from contact with the reactants as the reaction products are formed. This principle finds application in U.S. Pat. No. 3,450,500 to Setzer et al. which teaches a process for reforming hydrocarbon feedstocks and withdrawing the hydrogen product from contact with the feedstock driving the equilibrium to favor increased hydrogen production. Articles by Shu et al. and by Ziaka et al. teach that the extent of reaction for equilibrium dehydrogenation reactions may be further driven to product olefin by the concomitant removal of the hydrogen formed with hydrogen selective membranes. The article by Shu et al. appears in the *Canadian Journal of Chemical Engineering*, 69, 1036–1060 (1991); and the article by Ziaka et al. entitled "A High Temperature Catalytic Membrane Reactor for Propane Dehydrogenation" appears in the *Journal of Membrane Science*, 77, 221–232 (1993).

Similarly, British Patent Application GB 2190397A describes a process for producing aromatic hydrocarbons by catalytic paraffin dehydrocyclodimerization. The process upgrades $C_2$-$C_6$ paraffins, i.e., ethane, propane, butane or a mixture thereof to a mixture of aromatic hydrocarbons and hydrogen by-product in a reactor provided with a membrane capable of selective, in-situ transfer of at least a portion of the hydrogen in the mixture across the membrane. Catalysts useful in the paraffin upgrading process are said to include zeolites, and in particular gallium-containing zeolites.

It is believed that the paraffin dehydrogenation reaction is equilibrium limited when carried out in a conventional reactor due to the thermodynamics of equilibrium dehydrogenation. For example, at 550° C. the equilibrium propylene from propane dehydrogenation, irrespective of catalyst, is limited to 33%. Thus, the state of the art of endothermic hydrogen-producing paraffin upgrading processes would clearly be advanced by a process and apparatus for increasing the extent of reaction while also providing a high temperature heat source to supply at least a portion of the endothermic heat of reaction.

SUMMARY

There is provided a process for selective hydrogen combustion which comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering Selective hydrogen combustion product.

There is further provided a process for converting an alkane of the formula, $$C_nH_{2n+2},$$

to an alkene of the formula, $$C_nH_{2n},$$

where n is the same for said alkane and said alkene and n is from 2 to 5, said process comprising the steps of:
(a) contacting said alkane with a solid material comprising a dehydrogenation catalyst under conditions sufficient to produce said alkene and $H_2$;
(b) contacting a first stream comprising effluent from step (a) and a second stream comprising oxygen with separate surfaces of a membrane impervious to non-oxygen containing gases under conditions sufficient to selectively convert said $H_2$ to water, wherein said membrane comprises a metal oxide selective for hydrogen combustion; and
(c) contacting at least a portion of effluent from step (b) with a solid material comprising a dehydrogenation catalyst under conditions sufficient to convert unreacted alkane to additional quantities of said alkene and $H_2$.

DETAILED DESCRIPTION OF THE INVENTION

Figure 1:
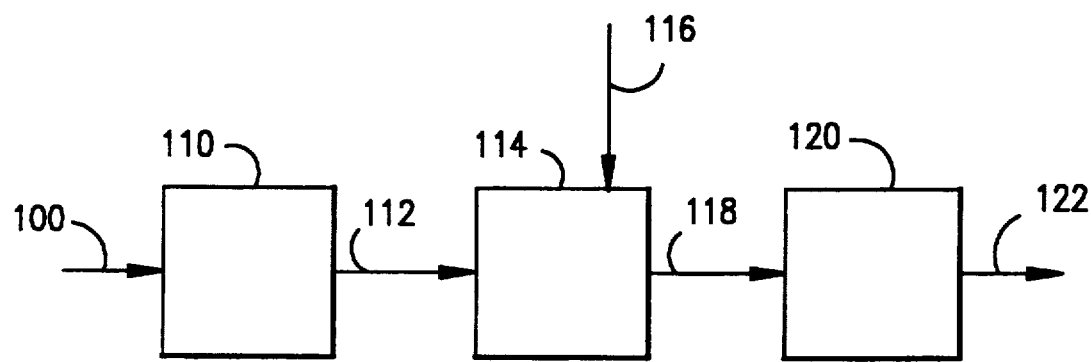
FIG. 1 provides a schematic diagram of an example of the present process, wherein a first dehydrogenation reactor is connected in series to a selective hydrogen combustion recator which is, in turn, connected to a second dehydrogenation reactor.

The selective hydrogen combustion process of the present invention can be used in a wide range of chemical processes. The selective hydrogen combustion process can be used to scavenge hydrogen out of the effluent stream of a catalytic dehydrogenation reactor and also supply part of the dehydrogenation heat requirement. For example, it can be used in place of or in addition to interstage heating. It can also be used as a combined dehydrogenation/selective hydrogen combustion process by using a conventional dehydrogenation catalyst bed inside a membrane structure containing a metal oxide selective for hydrogen combustion.

In the process of the present invention, by supplying sufficient oxygen to one side of a membrane being substantially impervious to non-oxygen containing gases and containing a selective hydrogen combustion metal oxide with high lattice oxygen conductivity, such as $Bi_2O_3$, the reacting surface of the metal oxide can remain essentially fully oxidized, while it is delivering its lattice oxygen to the gas phase hydrogen. The lattice oxygen is continuously being consumed on the feed side by the selective hydrogen combustion reaction and is continuously being replenished on the oxidant side by the reoxidation of the metal oxide. Evaporation of the reduced metal to the gas phase and the potential contamination of the dehydrogenation catalyst can be avoided.

The invention provides a membrane structure containing a reducible metal oxide useful in the selective hydrogen combustion of a hydrocarbon/hydrogen reactant feedstream. Generally, the hydrocarbon/hydrogen ratio is in the range of from about 0.1 to about 10. The membrane is substantially impervious to non-oxygen containing gases, i.e., those gases which contain molecules comprising elements other than oxygen, such as the hydrocarbon reactant gas as well as those which include oxygen atoms in the form of a gaseous compound. The membrane does, however, permit the conveyance of a form of oxygen via the membrane.

In accordance with the invention, a hydrocarbon/hydrogen reactant gas, such as styrene/hydrogen, is passed through, for example, a tubular membrane structure contacting the inner membrane surface. The outer surface of the membrane tube is contacted with an oxygen-containing gas, such as air. A gaseous product stream comprising water is formed. The reducible metal oxide of the membrane structure preferentially oxidizes the hydrogen in the presence of the hydrocarbons, such that an equivalent $H_2$/hydrocarbon mixture is converted to a mixture containing not more than about 9% hydrogen, the remaining hydrogen having been converted to $H_2O$. The process of the present invention operates in a continuous mode and at steady state. The metal oxide selective for hydrogen combustion is not reduced to a point where it is ineffective for selectively oxidizing hydrogen. The lattice oxygen of the $Bi_2O_3$ is continuously being replenished by air oxidation. The oxidation state of the metal oxide remains stable and the metal oxide of the present invention requires no further regeneration.

The present invention provides a membrane containing a selective hydrogen combustion catalyst comprising a reducible metal oxide in an amount in the range of from about 1% to about 100% by weight, and preferably in the range of from about 1% to about 10% by weight, supported on a porous ceramic support. Known ceramic materials such as alumina may be employed.

Selective combustion of hydrogen over hydrocarbons, such as alkanes or alkenes, is not a property common to all reducible metal oxides but rather is limited over a fairly narrow selection of metal oxides found to possess this particularly selective hydrogen combustion capability.

The oxides of bismuth are particularly selective for hydrogen combustion over hydrocarbon combustion, while the oxides of vanadium are not.

The metal oxide described herein may be an oxide of a single metal, such as bismuth or antimony, or it may be a mixed metal oxide. An example of a mixed metal oxide is a compound of the following empirical formula $Bi_aSb_bTe_cA_dB_eC_fO_x$ where
A = La, Ce, Y, Ru, Fe, Co, Ni, Cu, Al, In, Ga, and/or Ge
B = Mo, W, Cr, Sn, Nb, Ta, and/or Ti
C = an alkali, an alkaline earth, Ag, and/or Tl
O = oxygen
where
a,b,c = 0 to 12
a+b+c > 0
d = 0 to 12
e = 0 to 12
f = 0 to 12
x = dictated by the oxidation states of the remaining elements.

Another example of a mixed metal oxide is a compound of the following empirical formula $A_aB_bC_cD_dO_x$ where
A = In, Tl, Zn, Pb, and/or a Rare Earth (preferred RE = Tb, Gd, Ce, Y, and/or La)
B = La, Ce, Y, Ru, Fe, Co, Ni, Cu, Al, In, Ga, and/or Ge
C = P, Mo, W, Cr, Sn, Nb, Ta, and/or Ti
D = an alkali, an alkaline earth, Ag, and/or Tl
O = oxygen
where
0 < a < 12
b = 0 to 12
c = 0 to 12
d = 0 to 12
e = 0 to 12
x = dictated by the oxidation states of the remaining elements.

The membrane of the invention can be made by various means. For example, the membrane of the invention can, if desired, be formed by a technique commonly referred to as "slip casting". In general, in slip casting, finely ground material in a liquid suspension, or slip, is poured into a porous mold which absorbs liquid and leaves a layer of the material deposited on the walls of the mold. When desired thickness of materials is obtained in the mold, excess liquid is poured out. The deposited casting is then allowed to dry before being removed for sintering and annealing, to produce a mechanically stable form. A conventional mold material, such as plaster, can be used.

Alternatively, a method of preparation in accordance with common and well known techniques such as tape casting, extrusion, or molding with a core such as by chemical vapor deposition or dip coating on a porous tube can, if desired, be utilized.

It is also understood that in a process utilizing the membrane structure of the present invention, the surface area of the membrane available relative to reactant volume for hydrogen combustion can be increased by the selection of an appropriate design of the structure containing the membrane. For example, the surface area can be increased by the use of membrane structure composed of multiple tubes.

The membrane for use in the process of the present invention can be fabricated into shapes or structures appropriate for various designs including, for example, tubular structures, baffles, and various manifold configurations, such as a honeycomb structure. The honeycomb structure provides an increase in the surface area of the membrane relative to the volume of the reactant gas.

In one embodiment of the present invention, the reactor configuration is in the form of an annular tube reactor having an inner tubular membrane. A hydrogen containing hydrocarbon stream, such as the effluent from a paraffin dehydrogenation reactor, is passed through the membrane tube and air is passed through the annular space. The hydrogen is selectively oxidized by the lattice oxygen of the $Bi_2O_3$ wall, and the lattice oxygen is continuously being replenished by air oxidation on the annular side and $O_2-$ migration through the lattice. This is a steady state process, since the oxidation state of the metal oxide remains stable. The process is also exothermic, releasing the heat of combustion of $H_2$.

In a second embodiment of the present invention, multiple tubular membrane structures are used in a shell and tube reactor configuration. The hydrocarbon/hydrogen stream is passed through the tube side and air is passed through the shell side, to replenish the lattice oxygen that is being used for the selective hydrogen combustion reaction.

In a third embodiment of the present invention the membrane structure is in the form of a monolith. The hydrocarbon/hydrogen mixture is passed through nonadjacent channels of the monolith, and air is passed through the surrounding channels, for example, in a checkerboard type arrangement.

The selective hydrogen combustion reactions of the present invention generally occur at temperatures in the range of from about 300° C. to about 850° C. and at pressures in the range of from about 1 atm to about 20 atm.

The selective hydrogen combustion reactor of the present invention is suitable for use in the production of olefins. The use of the selective hydrogen combustion reactor results in a higher per pass olefin yield. The incorporation of a selective hydrogen combustion reactor further results in a means for supplying the heat of dehydrogenation.

Alkanes are converted to olefins (and dienes) by an integrated process scheme which involves the direct equilibrium dehydrogenation of alkanes via known catalysts and the selective oxidation of the resulting hydrogen gas thus formed. The light paraffins which may be utilized for such reactions include $C_2-C_5$, such as propane and isobutane. As an illustrative example, the overall reaction scheme, demonstrated for propane oxidative dehydrogenation, is thus:

SCHEME A:

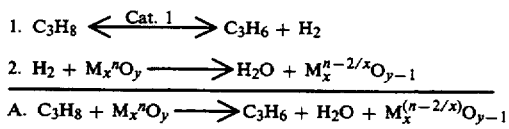

where the superscript of M denotes the oxidation state of the metal.

Reaction 1 is documented in the literature and is known as propane equilibrium dehydrogenation. Butane and isobutane equilibrium dehydrogenation are also known and documented in the literature. Reaction 1 has been demonstrated to occur catalytically over $Cr/Al_2O_3$, $Mo/Al_2O_3$, iron-based catalysts, supported (supports include silica, alumina, zirconia, titania, and thoria) and unsupported noble metals (e.g., Pt, Pd, Rh, Ir, Ru, etc), and supported and unsupported gallium and zinc oxides. Reaction 2 can proceed in the absence (redox mode), as opposed to the presence (cofed mode) of gaseous oxygen, over a number of reducible metal oxides. In the cofed mode, the reduced metal oxide is reoxidized in situ to its original state by the reaction:

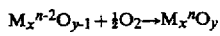

$$M_x{}^{n-2}O_{y-1} + \tfrac{1}{2}O_2 \rightarrow M_x{}^n O_y$$

Catalyst 1 and $M_x{}^n O_y$ may be used together or in separate reactors.

Several recent, open literature reports have discussed the oxidative dehydrogenation of propane and butane to the corresponding olefins. These reactions are typically carried out by utilizing a mixture of alkane and oxygen cofed over a metal oxide catalyst. Typical operating temperatures are from 400 to 600° C., 1-5 atm. pressure, either with a diluent or in the absence of one.

The present invention differs from the system described above in that the reaction involves two separately functioning catalysts-an equilibrium dehydrogenation catalyst, and a hydrogen combustion catalyst. These components may be used in separate reactors, connected in series or in a recycle mode, so as to drive the equilibration reaction (equation 1 above) further to the product side than is normally possible with only an equilibration catalyst. Thus, in the present scheme, the hydrogen would be combusted to H2O (or at least a portion of it), thus driving the equilibrium represented by equation 1 to the side of the products.

The catalyst used in the dehydrogenation reaction may be a known equilibrium dehydrogenation catalyst. Examples of such equilibrium dehydrogenation catalysts include (1) Pt, Pd, and other Group VIII metals either in bulk phase or supported on oxide supports (alumina, silica, titania, zirconia, zinc aluminate, etc.); (2) Cr, Mo (and their oxides) on oxide supports; (3) transition metal carbides and nitrides (molybdenum and tungsten carbides in particular); (4) nickel oxide or sulfide on oxide supports; (5) iron-based catalysts (e.g., in conjunction with chromia, potassia, etc.); (6) nickel calcium phosphate and other metal phosphates; and (7) gallium and zinc oxides either in bulk phase or supported on oxide supports. In addition, the dehydrogenation catalyst may be incorporated on the support in the manner illustrated for the reducible metal oxide.

By means of the present invention, whereby hydrogen is selectively oxidized after being produced in the dehydrogenation of an alkane, it is possible to obtain greater than equilibrium yields of alkenes from the overall process. The following table provides thermodynamic calculations of equilibrium yields of propylene, butene, and isobutene from propane, n-butane, and i-butane, respectively.

| Temperature, °C. | Propane | n-Butane | i-Butane |
|---|---|---|---|
| 350 | 2 | 3 | 4 |
| 400 | 4 | 7 | 8 |
| 450 | 9 | 15 | 18 |
| 500 | 18 | 28 | 33 |
| 550 | 32 | 46 | 53 |
| 600 | 50 | 66 | 72 |
| 650 | 68 | 82 | 85 |
| 700 | 82 | 92 | 93 |

FIG. 1 provides a schematic diagram of an example of the present process, wherein a first dehydrogenation reactor is connected in series to an oxidation reactor which is, in turn, connected to a second dehydrogenation reactor. In FIG. 1, a suitable alkane feed, such as propane, is introduced into dehydrogenation reactor 110 via line 100. The effluent from reactor 110, comprising alkene, hydrogen and unreacted alkane, passes through line 112 to the tube side of oxidation reactor 114, wherein hydrogen is selectively oxidized. Oxygen, e.g. in the form of air is introduced through line 116 to the shell side of reactor 114. The effluent from the oxidation reactor, comprising unreacted alkane, alkene and a reduced amount of hydrogen, then passes through line 118 to a second dehydrogenation reactor 120, wherein unreacted alkane from the first dehydrogenation reactor is converted to additional alkene and hydrogen. The product from reactor 120 may be recovered via line 122 or it may be passed via line 122 to one or more oxidation reactors, each followed by a dehydrogenation reactor connected in series.

Figure 2:
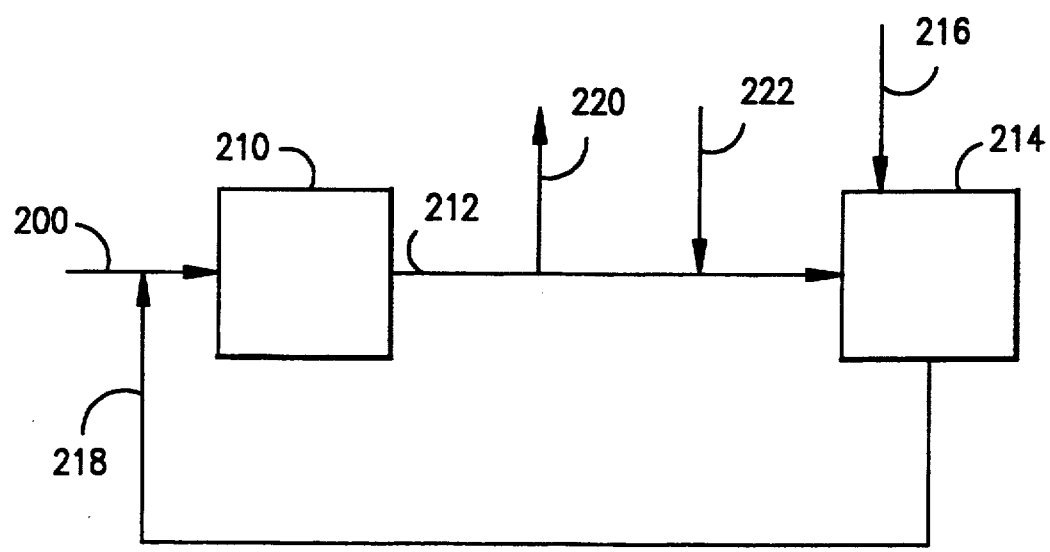
FIG. 2 provides a schematic diagram of an example of the present process, wherein a dehydrogenation reactor is connected to a selective hydrogen combustion reactor in a manner which facilitates recycle of the effluent from the selective hydrogen combustion reactor back into the dehydrogenation reactor.

FIG. 2 provides a schematic diagram of an example of the present process, wherein a dehydrogenation reactor is connected to an oxidation reactor in a manner which facilitates recycle of the effluent from the oxidation reactor back into the dehydrogenation reactor. In FIG. 2, a suitable alkane feed, such as propane, is introduced into dehydrogenation reactor 210 via line 200. The effluent from reactor 210, comprising alkene, hydrogen and unreacted alkane, passes through line 212 to the tube side of oxidation reactor 214, wherein hydrogen is selectively oxidized. Oxygen, e.g. in the form of air is introduced through line 216 to the shell side of reactor 214. The effluent from the oxidation reactor, comprising unreacted alkane, alkene and a reduced amount of hydrogen, then passes through recycle line 218 to line 200 and back into dehydrogenation reactor 210, wherein unreacted alkane from the first dehydrogenation reactor pass is converted to additional alkene and hydrogen. The number of passes or recycle steps through the system depends on the desired level of alkane conversion to alkene product. When a sufficient level of conversion is achieved, the product may be recovered via line 220 or it may be passed via line 220 to a series of one or more additional oxidation and dehydrogenation reactors.

The recycle reaction scheme shown in FIG. 2 may be operated in a batch or continuous mode. In the batch mode, the flow of fresh alkane feed to reactor 210 via line 200 is shut off at a certain point in time so that the recycle stream from line 222 becomes the only source of reactant in reactor 210. While this batch mode recycle reaction is taking place, line 220 remains closed. After a desired level of conversion is achieved, line 220 may be opened and product recovered. The introduction of a flush gas, such as nitrogen, into the system, e.g., via line 222, may facilitate recovery of the product.

In a continuous mode, line 220 may be partially opened so that a metered amount of product is withdrawn, while the remainder of the effluent from reactor 210 passes into the oxidation reactor 214 via line 212. As a portion of the product is being continuously withdrawn via line 220, a corresponding amount of fresh alkane feed is introduced into reactor 210 along with the recycle stream.

The following examples illustrate the process of the present invention.

EXAMPLE 1

An equimolar mixture of 15% hydrogen and 15% propylene in helium is flown through a porous alumina tube, 5 inches in length with ¼" outside diameter, the inner wall of which is coated with a contiguous layer of $Bi_2O_3$, 100 microns thick. The flow rate of the mixture is 100 cc/min and the temperature is 550° C. The composition of the effluent stream is analyzed with gas chromatography and is found to be 2% hydrogen and 14% propylene, while steam and small quantities of CO and $CO_2$ are also detected. As the hydrogen/propylene mixture passes through the tube, it contacts the $Bi_2O_3$ layer and the hydrogen present is selectively oxidized to water by virtue of the lattice oxygen of the metal oxide. The metal oxide layer is simultaneously oxidized by contact with air supplied to the exterior of the tube, which diffuses through the porous alumina tube wall and contacts the outside surface of the layer. This selective hydrogen combustion process is sustained for 24 hours and can be sustained indefinitely while air reoxidizes the $Bi_2O_3$ layer.

EXAMPLE 2

Three reactors are connected in series, the first and the third are fixed bed reactors, each loaded with 2.0 gr. Pt/Sn/ZSM-5 catalyst (0.65% Pt). The second reactor is the porous alumina tube with the $Bi_2O_3$ layer, described in Example 1. The temperatures of the three reactors are maintained at 550, 500 and 550° C. respectively. Propane is passed to the first reactor at a flow rate of 17 cc/min, while adequate supply of air is provided to the external surface of the porous second reactor. The gaseous effluent from the third reactor is analyzed by gas chromatography. The conversion of propane is 45%, yielding propylene at 39%, CO and $CO_2$ at 3% and hydrocracked byproducts at 3%. The effluent also contains equimolar amounts of hydrogen and water, the effluent water being generated in the second reactor by the SHC reaction. It is noted that the propylene yield obtained is higher than the equilibrium yield predicted for propane dehydrogenation at 550° C.

Changes and modifications in the specifically described embodiments can be carried out without departing from the scope of the present invention which is intended to be limited only by the scope of the appended claims.

What is claimed is:

1. A process for selective hydrogen combustion which comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product.

2. The process of claim 1, wherein the selective hydrogen combustion process is operated in a continuous mode.

3. The process of claim 1, wherein said metal oxide comprises $Bi_2O_3$.

4. The process of claim 1, wherein said metal oxide comprises a mixed metal oxide containing bismuth.

5. The process of claim 1, wherein said metal oxide comprises $In_2O_3$.

6. The process of claim 1, wherein said metal oxide comprises a mixed metal oxide containing indium.

7. The process of claim 1, wherein said metal oxide comprises $Sb_2O_3$.

8. The process of claim 1, wherein said metal oxide comprises a mixed metal oxide containing antimony.

9. The process of claim 1, wherein said metal oxide comprises $Tl_2O_3$.

10. The process of claim 1, wherein said metal oxide comprises a mixed metal oxide containing thallium.

11. The process of claim 1, wherein said metal oxide comprises ZnO.

12. The process of claim 1, wherein said metal oxide comprises a mixed metal oxide containing zinc.

13. A process for converting an alkane of the formula, $$C_nH_{2n+2},$$

to an alkene of the formula, $$C_nH_{2n},$$

where n is the same for said alkane and said alkene and n is from 2 to 5, said process comprising the steps of:
   (a) contacting said alkane with a solid material comprising a dehydrogenation catalyst under conditions sufficient to produce said alkene and $H_2$;
   (b) contacting a first stream comprising effluent from step (a) and a second stream comprising oxygen with separate surfaces of a membrane impervious to non-oxygen containing gases under conditions sufficient to selectively convert said $H_2$ to water, wherein said membrane comprises a metal oxide selective for hydrogen combustion; and
   (c) contacting at least a portion of effluent from step (b) with a solid material comprising a dehydrogenation catalyst under conditions sufficient to convert unreacted alkane to additional quantities of said alkene and $H_2$.

14. The process of claim 13, wherein said metal oxide comprises $Bi_2O_3$.

15. The process of claim 13, wherein said metal oxide comprises a mixed metal oxide containing bismuth.

16. The process of claim 13, wherein said metal oxide comprises $In_2O_3$.

17. The process of claim 13, wherein said metal oxide comprises a mixed metal oxide containing indium.

18. The process of claim 13, wherein said metal oxide comprises $Sb_2O_3$.

19. The process of claim 13, wherein said metal oxide comprises a mixed metal oxide containing antimony.

20. The process of claim 13, wherein said metal oxide comprises $Tl_2O_3$.

21. The process of claim 13, wherein said metal oxide comprises a mixed metal oxide containing thallium.

22. The process of claim 13, wherein said metal oxide comprises ZnO.

23. The process of claim 13, wherein said metal oxide comprises a mixed metal oxide containing zinc.

24. The process of claim 13, wherein said dehydrogenation catalyst comprises platinum.

25. The process of claim 13, wherein step (a) and step (b) are conducted in one reaction zone.

26. The process of claim 25, wherein said membrane comprises said dehydrogenation catalyst.

27. The process of claim 13, wherein step (a) is conducted in a separate reaction zone from step (b).

28. A process for converting an alkane of the formula, $$C_nH_{2n+2},$$

to an alkene of the formula, $$C_nH_{2n},$$

where n is the same for said alkane and said alkene and n is from 2 to 5, said process comprising the steps of:
(a) contacting said alkane with a solid material comprising a dehydrogenation catalyst under conditions sufficient to produce said alkene and $H_2$;
(b) contacting a first stream comprising a first portion of effluent from step (a) and a second stream comprising oxygen with separate surfaces of a membrane impervious to non-oxygen containing gases under conditions sufficient to selectively convert said $H_2$ to water, wherein said membrane comprises a metal oxide selective for hydrogen combustion; and
(c) recycling effluent from step (b) to step (a); and
(d) withdrawing a second portion of effluent from step (a) as product.

29. The process of claim 28, wherein step (a) and step (b) are conducted in one reaction zone.

30. The process of claim 29, wherein said membrane comprises said dehydrogenation catalyst.

31. The process of claim 28, wherein said metal oxide comprises $Bi_2O_3$.

32. The process of claim 28, wherein said metal oxide comprises a mixed metal oxide containing bismuth.

33. The process of claim 28, wherein said metal oxide comprises $In_2O_3$.

34. The process of claim 28, wherein said metal oxide comprises a mixed metal oxide containing indium.

35. The process of claim 28, wherein said metal oxide comprises $Sb_2O_3$.

36. The process of claim 28, wherein said metal oxide comprises a mixed metal oxide containing antimony.

37. The process of claim 28, wherein said metal oxide comprises $Tl_2O_3$.

38. The process of claim 28, wherein said metal oxide comprises a mixed metal oxide containing thallium.

39. The process of claim 28, wherein said metal oxide comprises ZnO.

40. The process of claim 28, wherein said metal oxide comprises a mixed metal oxide containing zinc.

41. The process of claim 28, wherein said dehydrogenation catalyst comprises platinum.

* * * * *